(12) United States Patent
Muraishi et al.

(10) Patent No.: US 7,465,588 B2
(45) Date of Patent: Dec. 16, 2008

(54) APPARATUS AND METHOD OF ASSAY IN UTILIZING ATTENUATED TOTAL REFLECTION

(75) Inventors: Katsuaki Muraishi, Kanagawa (JP); Nobuhiko Ogura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 407 days.

(21) Appl. No.: 11/239,202

(22) Filed: Sep. 30, 2005

(65) Prior Publication Data
US 2006/0068489 A1 Mar. 30, 2006

(30) Foreign Application Priority Data
Sep. 30, 2004 (JP) .............................. 2004-288539

(51) Int. Cl.
*G01N 33/553* (2006.01)
(52) U.S. Cl. .................. 436/525; 385/12; 385/129; 385/130; 422/82.05; 422/82.11; 435/288.7; 435/808; 436/164; 436/524; 436/805
(58) Field of Classification Search .................. None
See application file for complete search history.

(56) References Cited

U.S. PATENT DOCUMENTS

| 5,313,264 | A |  | 5/1994 | Ivarsson et al. |  |
|---|---|---|---|---|---|
| 5,822,073 | A |  | 10/1998 | Yee et al. |  |
| 5,965,456 | A | * | 10/1999 | Malmqvist et al. | .......... 436/514 |
| 6,330,062 | B1 | * | 12/2001 | Corn et al. | .................. 356/445 |
| 7,037,727 | B1 | * | 5/2006 | Miura et al. | ................. 436/518 |
| 7,267,797 | B1 | * | 9/2007 | Craighead et al. | ......... 422/82.05 |

FOREIGN PATENT DOCUMENTS

| JP | 61-292540 A | 12/1986 |
|---|---|---|
| JP | 4-501462 A | 3/1992 |
| JP | 6-167443 A | 6/1994 |
| WO | WO 90/05293 A | 5/1990 |

OTHER PUBLICATIONS

Cheskis, B. and Freedman, L. P., Modulation of Nuclear Receptor Interactions by Ligands: Kinetic Analysis Using Surface Plasmon Resonance, Biochemistry, 1996, pp. 3309-3318, vol. 35, No. 10, American Chemical Society, Easton, PA. XP002066531. ISSN: 0006-2960.

* cited by examiner

*Primary Examiner*—Christopher L Chin
(74) *Attorney, Agent, or Firm*—Sughrue Mion, PLLC

(57) ABSTRACT

An assay apparatus is loaded with a sensor unit as surface plasmon resonance (SPR) biosensor, which includes a transparent dielectric medium and thin film. A first surface of the thin film is a thin film/dielectric interface. Its sensing surface causes reaction of sample fluid. An optical assay unit assays reaction of the sample fluid by detecting illuminating light reflected by the interface. Measured data from the optical assay unit is compared with a reference parameter, to evaluate suitability of the measured data for analysis. If lack of the suitability is estimated in the evaluation, a succeeding density of the sample fluid to be used in a succeeding evaluating assay is determined according to the measured data with the estimated lack of the suitability. The sample fluid is prepared at the succeeding density by mixing with diluent fluid, and then is used for the succeeding evaluating assay.

18 Claims, 7 Drawing Sheets

APPARATUS AND METHOD OF ASSAY IN UTILIZING ATTENUATED TOTAL REFLECTION

BACKGROUND OF THE INVENTION

1. Field of the Invention

The present invention relates to an apparatus and method of assay in utilizing attenuated total reflection. More particularly, the present invention relates to an apparatus and method of assay in utilizing attenuated total reflection, in which density of analyte fluid can be adjusted with high precision, and thus analysis of interaction between ligand and the analyte can be easy with a high throughput by raising precision in retrieval of a reaction curve.

2. Description Related to the Prior Art

An assay apparatus in utilizing attenuated total reflection for assaying a sample is known in the field of the biosensor. U.S. Pat. No. 5,313,264 (corresponding to JP-A 4-501462) discloses a surface plasmon resonance (SPR) sensor as a typical example for this assay.

A thin film, or metal film, is formed on a transparent dielectric medium. One surface of the metal film is a sensing surface where reaction of a sample occurs. Another surface of the metal film is a metal/dielectric interface where light is applied by satisfying a condition of total reflection. The reaction is detected to assay the sample according to attenuation of the reflected light from the metal/dielectric interface. The surface plasmon resonance (SPR) assay apparatus is constructed to detect surface plasmon resonance created on the sensing surface which is the first surface of the metal film.

Surface plasmon is a term to mean the compressional wave created on the surface of the metal and included in plasmon as quantized expression of the compressional wave. In a metal, free electrons vibrate to generate the compressional wave called a plasma wave. The surface plasmon travels along the surface of the metal.

Light for detection is applied to a metal/dielectric interface of the metal film that is back to the sensing surface so that the total reflection condition is satisfied, namely at an angle of incidence equal to or more than a critical angle. In addition to the total reflection created on the metal/dielectric interface, a small component of the light passes through the metal film without reflection, and penetrates to the sensing surface. A wave of the penetrating component is called an evanescent wave. Surface plasmon resonance (SPR) is created when frequency of the evanescent wave coincides with that of the surface plasmon. In response to this, intensity of the reflected light attenuates remarkably. In the assay apparatus, the attenuation in the reflected light reflected by the metal/dielectric interface is detected, to recognize creation of the SPR on the sensing surface.

The angle of incidence, namely resonance angle of the light to generate the SPR depends on the refraction index of the transmission medium transmitting evanescent wave and surface plasmon. In other words, a change in the resonance angle to create SPR changes in response to a change in the refraction index of the transmission medium. The substance contacting the sensing surface is a transmission medium transmitting the evanescent wave and surface plasmon. If binding or dissociation between two molecules occurs on the sensing surface, the resonance angle changes because of a change in the refraction index of the transmission medium. In the SPR system, the change in the refraction index is detected, to measure interaction of molecules.

The assay apparatus can be used for various kinds of studies in a biochemical field or the like, for example to study interaction of protein, DNA and various biomaterials, and to select candidate drugs by screening. Also, the technique is useful in the fields of the clinical medicine, food industries and the like. It is possible to use one of two substances as a ligand and another of them as an analyte if those have bioaffinity. For the purpose of screening, protein as biomaterial is used as ligand. Candidate drugs are discretely used as analyte, and contacted with the ligand on the sensing surface, to study interaction.

JP-A 6-167443 and U.S. Pat. No. 5,822,073 disclose discloses an SPR assay apparatus in which an optical system of Kretschmann configuration is used for incidence of light to the metal film. According to the Kretschmann configuration, the surface of the metal film as metal/dielectric interface is fitted on a prism, which condenses light and directs the light to the metal/dielectric interface in a manner conditioned for total reflection. A sample or ligand is immobilized on the sensing surface. A flow channel is formed to have the sensing surface inside, and causes analyte fluid to flow. The analyte fluid is introduced in the flow channel to flow, and is caused to contact the ligand. Interaction between the analyte fluid and the ligand is assayed by detecting surface plasmon resonance created during the reaction.

In the surface plasmon resonance (SPR) assay, interaction between the ligand and analyte on the sensing surface can be output rapidly as an output signal. A reaction speed constant is obtained by use of a reaction curve which represents changes of the output signal with time. The interaction between the ligand and analyte can be analyzed with the reaction speed constant in a time sequential manner. To obtain the reaction speed constant, the reaction curve according to the measurement is subjected to curve fitting based on the calculation, for example non-linear least squares fitting.

Forms of the reaction curve suitable for the curve fitting are known according to various experimental attempts. For the purpose of obtaining an optimized form of the reaction curve, density of analyte solution or analyte liquid is changed in a stepwise manner, to measure an output signal of the surface plasmon resonance (SPR).

If unknown compounds are treated for measurement, for example drug screening, possibility of reaction itself is not known initially. To this end, the analyte solution or analyte liquid of a high density is prepared to measure the compounds, to check occurrence or lack of reaction. If reaction occurs, the analyte liquid of a second density lower than the first density is prepared, to measure the compound for the second time. For example, an initial rise of the signal in an early section can be too high. In this situation, the analyte liquid of a third density lower than the second density is prepared, to measure the compound for the third time. According to repeated experiments, an optimized form of the reaction curve is obtained finally. After the successful result of the optimization, the curve fitting is made according to the reaction curve, to find the reaction speed constant.

Calculating processes of the curve fitting are known in the art. The reaction speed constant may be obtained readily by utilizing software of arithmetic processing only if the reaction curve can be optimized.

However, determination of density of the analyte solution or analyte liquid and preparation of the analyte liquid have been based on skills of technicians conducting experiments for the purpose of optimizing the reaction curve for the curve fitting. Errors in observation, estimation and calculation of the technicians are very likely to occur according to specifically personal skills. This leads to a long time analysis or an erroneous result of the analysis, which is very unsuitable for assay with high precision.

SUMMARY OF THE INVENTION

In view of the foregoing problems, an object of the present invention is to provide an apparatus and method of assay in utilizing attenuated total reflection, in which density of analyte fluid can be adjusted with high precision, and thus analysis of interaction between ligand and the analyte can be easy with a high throughput by raising precision in retrieval of a reaction curve.

In order to achieve the above and other objects and advantages of this invention, an assay apparatus for assay in utilizing attenuated total reflection by use of at least one sensor unit is provided, the sensor unit including a transparent dielectric medium, and thin film, having a first surface and a sensing surface reverse thereto, the first surface overlying on the dielectric medium to constitute a thin film/dielectric interface, the sensing surface causing reaction of sample fluid, and having an optical assay unit for applying illuminating light to the interface through the dielectric medium in such a form as to satisfy a total reflection condition, and for deriving information of reaction of the sample fluid by detecting the illuminating light reflected by the interface. The assay apparatus includes a fluid processor for preparing the sample fluid at a density by mixing with diluent fluid. An evaluator is responsive to an evaluating assay in using the sample fluid prepared by the fluid processor, for comparing measured data output by the optical assay unit with a reference parameter stored in a data storage, in order to evaluate suitability of the measured data for analysis. A density determiner is responsive if the evaluator estimates lack of the suitability, for determining a succeeding density of the sample fluid to be used in a succeeding evaluating assay according to the measured data with the estimated lack of the suitability. The fluid processor prepares the sample fluid at the succeeding density determined by the density determiner, for the succeeding evaluating assay according to the succeeding density of the sample fluid.

Preferably, the sample fluid is analyte, and the sensing surface causes interaction of ligand with the analyte.

Furthermore, a controller is in operation until the evaluator judges that the measured data from the optical assay unit is suitable, for repeatedly carrying out the evaluating assay with the sample fluid at the density determined by the density determiner.

Preferably, the sensor unit includes plural sensor cells, each of which is constituted by the sensing surface and a flow channel for flow of the sample fluid on the sensing surface. The fluid processor, the evaluator and the density determiner operate for each of the sensor cells.

Preferably, the sensor unit includes a flow channel block, provided with the dielectric medium secured thereto, and having the flow channel of the plural sensor cells, oriented to receive the sensing surface, for causing the sample fluid to flow on the sensing surface.

Furthermore, a constant determiner is responsive if the evaluator estimates the suitability, for determining a reaction speed constant of the sample fluid by curve fitting according to the measured data with the suitability.

Preferably, there is a data analyzer, positioned separately from the fluid processor, for accommodating the evaluator, the density determiner, and the constant determiner.

Preferably, the fluid processor includes a sample fluid reservoir for storing the sample fluid. A diluent reservoir stores the diluent fluid. A mixer accesses the sample fluid reservoir and the diluent reservoir and for producing mixture thereof.

Preferably, the reference parameter is a gradient of a reaction curve optimized for the curve fitting.

Preferably, the reference parameter is at least one selected from a gradient of a reaction curve, an absolute value of a signal level in an initial step in reaction, and time required for creating a stable state of the signal level.

Preferably, the evaluator compares the reference parameter with a gradient of a reaction curve created according to the measured data, to estimate suitability of the measured data.

Preferably, the density determiner considers a gradient A of the reaction curve according to the measured data, and a gradient B constituted by the reference parameter, and determines the succeeding density by multiplying the density by a value of a ratio B/A.

Furthermore, a fluid dispenser discharges the sample fluid from the fluid processor. A sensor setting mechanism moves one of the sensor unit and the fluid dispenser relative to a remaining one thereof, to set the fluid dispenser at one of the sensor cells in the sensor unit. A fluid transfer mechanism introduces the sample fluid being prepared to the one sensor cell through the fluid dispenser.

Preferably, the sensor unit further includes a flow channel block, having a flow channel, oriented to receive the sensing surface at the flow channel, for causing the sample fluid to flow on the sensing surface upon being introduced. A prism is positioned between the flow channel block and the optical assay unit, for constituting the transparent dielectric medium, and for passing the illuminating light reflected by the interface in the total reflection.

In one preferred embodiment, the sensor unit is a chip type. Furthermore, a flow channel block is secured to the sensor unit on a side of the thin film, having a flow channel, oriented to receive the sensing surface at the flow channel, for causing the sample fluid to flow on the sensing surface upon being introduced. A prism is positioned at the sensor unit on the transparent dielectric medium, for constituting the optical assay unit, and for passing the illuminating light reflected by the interface in the total reflection.

Preferably, the thin film is metal film, and is responsive to incidence of the illuminating light, to generate surface plasmon resonance on the sensing surface.

According to one aspect of the invention, an assay method of assay in utilizing attenuated total reflection by use of at least one sensor unit is provided. There is an outputting step of outputting measured data from the optical assay unit. In an evaluating step, the measured data is compared with a reference parameter stored in a data storage, in order to evaluate suitability of the measured data for analysis. In a density determining step, if lack of the suitability is estimated in the evaluating step, a succeeding density of the sample fluid to be used in a succeeding evaluating assay is determined according to the measured data with the estimated lack of the suitability. In a fluid preparing step, the sample fluid is prepared at the succeeding density by mixing with diluent fluid. The sample fluid prepared in the fluid preparing step is used for the succeeding evaluating assay.

Preferably, until it is judged in the evaluating step that the measured data from the optical assay unit is suitable, the evaluating assay with the sample fluid is repeatedly carried out at the density determined in the density determining step.

Furthermore, if the suitability is estimated in the evaluating step, a reaction speed constant of the sample fluid is determined by curve fitting according to the measured data with the suitability.

Furthermore, one of the sensor unit and a fluid dispenser is moved relative to a remaining one thereof. The fluid dispenser is set at one of the sensor cells in the sensor unit. The sample fluid after being prepared introduced to the one sensor cell through the fluid dispenser.

Accordingly, density of analyte fluid can be adjusted with high precision because of the automated feedback control of the preparation of the analyte fluid. Analysis of interaction between ligand and the analyte can be easy with a high throughput by raising precision in retrieval of a reaction curve.

BRIEF DESCRIPTION OF THE DRAWINGS

The above objects and advantages of the present invention will become more apparent from the following detailed description when read in connection with the accompanying drawings, in which.

DETAILED DESCRIPTION OF THE PREFERRED EMBODIMENT(S) OF THE PRESENT INVENTION

Figure 1A:
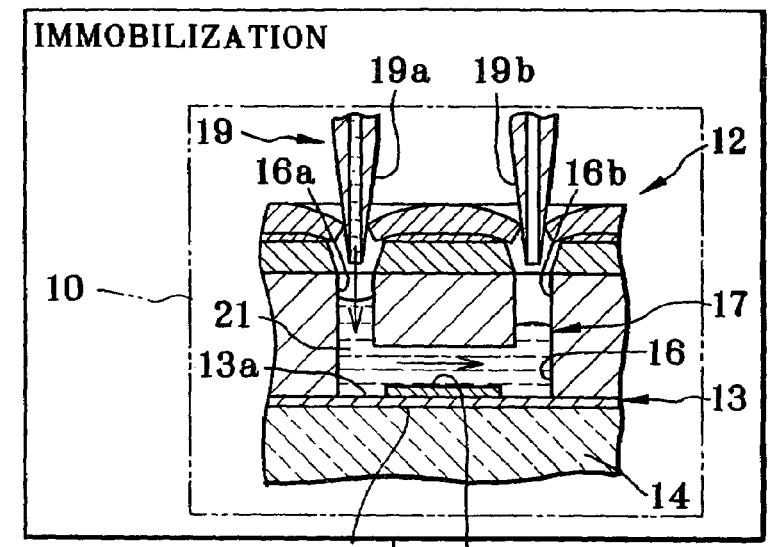
FIG. 1A is a section, partially broken, illustrating a sample immobilizing step included in an assay method of a surface plasmon resonance biosensor.
Figure 1B:
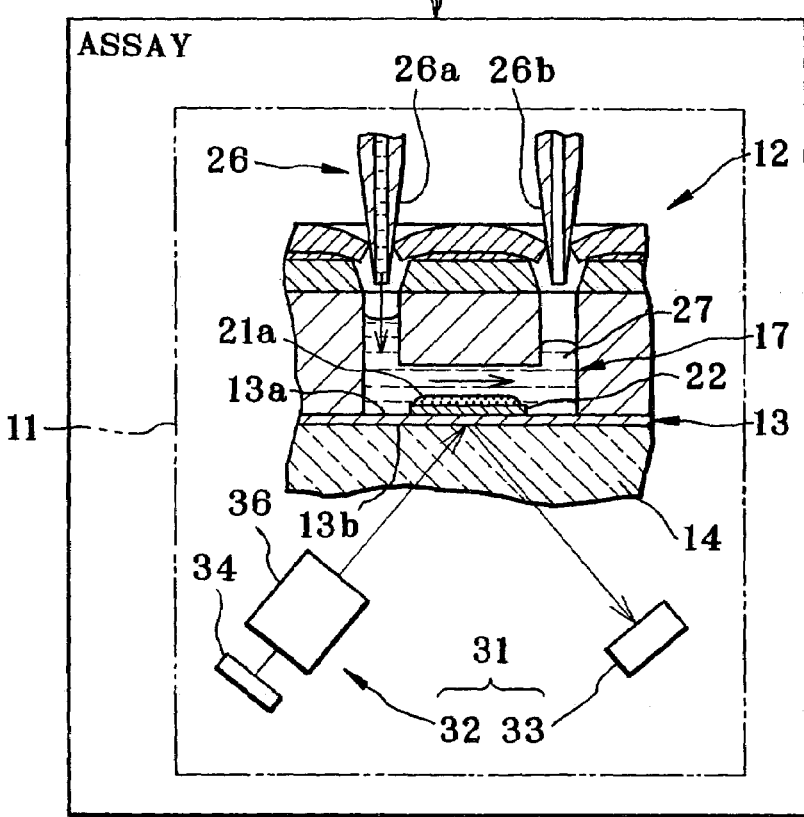
FIG. 1B is a section, partially broken, illustrating an assay step included in the assay method.
Figure 4:
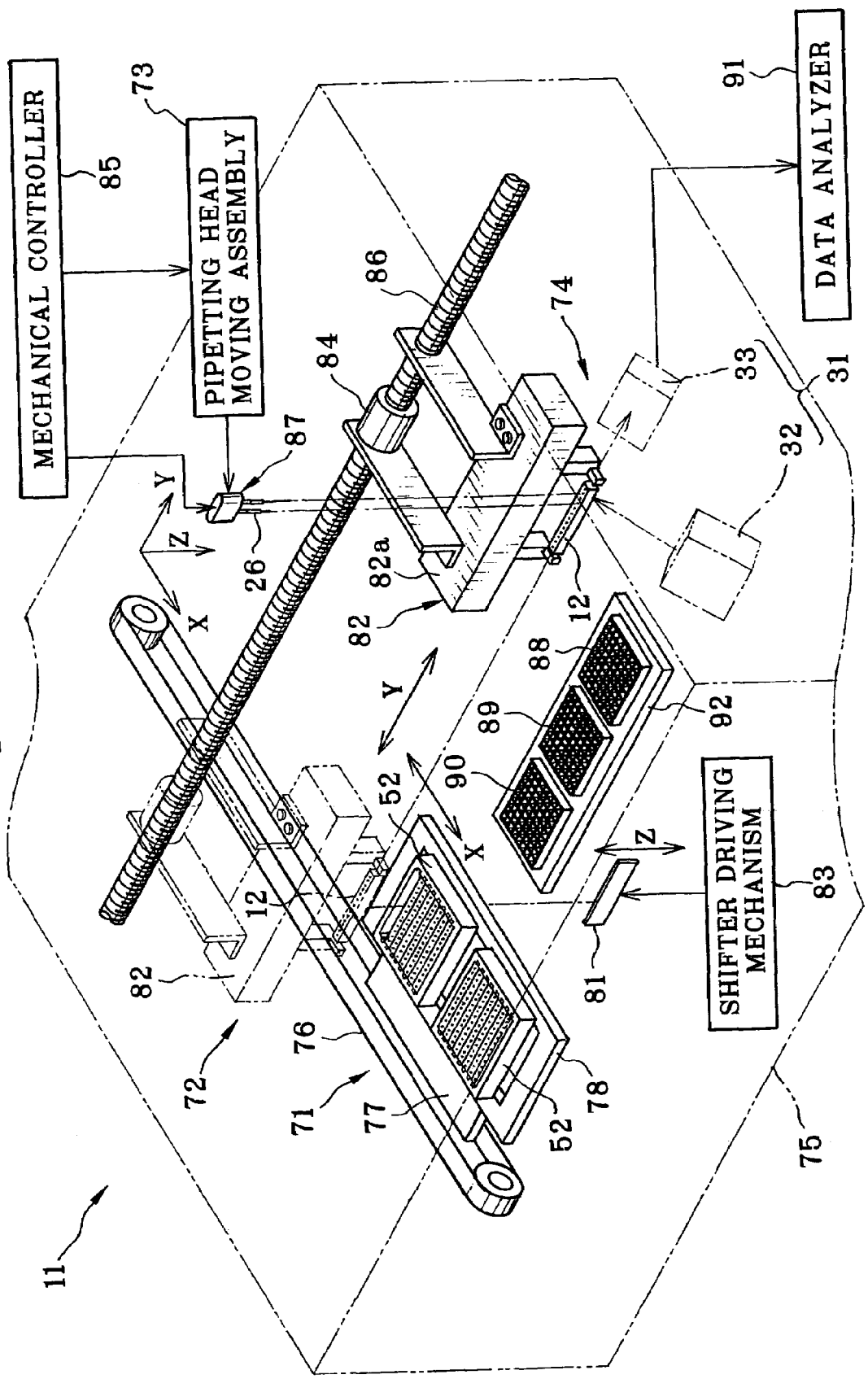
FIG. 4 is a perspective view illustrating an assay apparatus.

In FIGS. 1A and 1B, a system for measuring or assay according to SPR (surface plasmon resonance) is illustrated. A sequence of the assay system is constituted by three processes which are a sample immobilizing process, assay process and data analyzing process. The assay system includes a sample immobilizing device 10, an assay apparatus 11, and a data analyzer 91, which is illustrated in FIG. 4.

A surface plasmon resonance (SPR) biosensor is used as a sensor unit 12 for assay. The sensor unit 12 includes a metal film 13, a prism 14 and a flow channel block 41. A first surface of the metal film 13 is a sensing surface 13a where surface plasmon resonance is created. A second surface of the metal film 13 is a thin film/dielectric interface or light entrance surface 13b where the prism 14 is overlaid therewith. The flow channel block 41 has a flow channel 16, which extends along the sensing surface 13a, and causes ligand and analyte as fluids to flow.

An example of material for the metal film 13 is gold (Au). A thickness of the metal film 13 is 50 nm. The thickness can be changed for the suitability in view of the material of the metal film 13, a wavelength of light to be applied, and the like. The prism 14 is a transparent dielectric medium or block, overlaid with the metal film 13, and also is an optical element for condensing light toward the thin film/dielectric interface 13b for satisfying the condition of the total reflection. The flow channel 16 is a U-shaped conduit, and has an entrance end opening 16a and an exit end opening 16b. A diameter of the flow channel 16 is approximately 1 mm. An interval between the entrance end opening 16a and the exit end opening 16b is approximately 10 mm.

A lower side of the flow channel 16 is open initially, but closed in a firmly enclosed manner by covering of the sensing surface 13a. Sensor cells 17 are constituted by combinations of the flow channel 16 and the sensing surface 13a. The sensor unit 12 includes a plurality of the sensor cells 17. See FIG. 2. This will be described later in detail.

The immobilizing process is a binding step of ligand on the sensing surface 13a. At first, the sensor unit 12 is set in the sample immobilizing device 10. A pipette couple 19 is included in the sample immobilizing device 10, and has dispensing and removing pipettes 19a and 19b. The pipette 19a is set at the entrance end opening 16a. The pipette 19b is set at the exit end opening 16b. The pipette 19a introduces liquid to the flow channel 16. The pipette 19b sucks and removes liquid from the flow channel 16. The introduction with the pipette 19a is at the same time as the removal with the pipette 19b. Ligand solution or ligand fluid 21, as a fluid which contains ligand or biomaterial and fluid medium, is introduced through the entrance end opening 16a by the pipette couple 19.

A linker film 22 is overlaid on a middle portion of the sensing surface 13a for binding with the ligand. In the manufacturing process of the sensor unit 12, the linker film 22 is formed. As the linker film 22 is a basis for immobilizing the ligand, a material for the linker film 22 is selectively determined.

Pre-treatment before immobilization with the ligand fluid 21 is wetting of the linker film 22 by use of liquid buffer, and activation of the linker film 22 for the purpose of facilitating binding of the ligand to the linker film 22. An example of a method is the amine coupling method. An example of material for the linker film 22 is carboxy methyl dextran, to bind an amino group contained in the ligand with the dextran directly by a covalent bond. An example of liquid for the activation is mixture of N'-(3-dimethylaminopropyl) carbodiimide hydrochloride (EDC) and N-hydroxy imide succinate (NHS). After the activation, liquid buffer for immobilization is introduced to wash and clean the flow channel 16.

Various liquids are available for use as the liquid buffer for immobilization, and solvent or diluent for the ligand fluid 21. Examples of the liquids include buffer liquids, or physiological saline water and other aqueous solutions of physiological salts, and pure water. It is possible according to a type of the ligand to determine suitably solution types and pH values of the solutions, and types of substances to be mixed, and their density. If a biomaterial is used as a ligand, physiological saline water is used of which pH value is kept neutralized. In the amine coupling method described above, the linker film 22 is electrified negatively because of the carboxy methyl dextran. In consideration of this, it is possible to use phosphate buffered saline (PBS) solution having strong operation of buffer and containing phosphate salt at high density which is not physiological, because protein can be electrified positively for the purpose of facilitating binding with the linker film 22.

After the activation and washing, the ligand fluid 21 is introduced to the sensor cells 17 for a ligand immobilizing process. Ligand or sample 21a such as biomaterial diffused in the ligand fluid 21, in introducing the ligand fluid 21, gradually comes near to and binds with the linker film 22. This is immobilization of the ligand 21a on the sensing surface 13a. It is general that a step of the immobilization requires approximately one (1) hour, during which the sensor unit 12 is preserved in an environment conditioned suitably, for example at a conditioned temperature. In the course of the immobilization, the ligand fluid 21 in the flow channel 16 may be left to stand in a stationary state. However, the ligand fluid 21 can be preferably stirred or turbulently flowed for ensured fluidity in the flow channel 16. The stirring or turbulent flow can promote binding of the ligand 21a with the linker film 22, to raise an immobilized amount of the ligand 21a.

When the immobilization of the ligand 21a on the sensing surface 13a is completed, then the ligand fluid 21 is removed from the flow channel 16. The pipette 19b discharges the ligand fluid 21 by suction. After this, the sensing surface 13a is washed by feeding washing liquid into the flow channel 16. A blocking step, if required, is added after the washing. A blocking liquid is introduced into the flow channel 16, to render inactive the reaction group remaining without binding with the ligand. A preferable example of the blocking liquid is ethanol amine hydrochloride. After the blocking, the flow channel 16 is washed again. Then evaporation retardant is introduced to the flow channel 16, which will be described in detail later. The sensor unit 12 remains preserved until the assay with the sensing surface 13a humid on the evaporation retardant.

For the assay process, the sensor unit 12 is set in the assay apparatus 11. A pipette couple 26 is disposed in the assay apparatus 11 in the same manner as the pipette couple 19 in the sample immobilizing device 10. The pipette couple 26 introduces liquid of several types into the flow channel 16 through the entrance end opening 16a. At first, liquid buffer for assay is introduced into the flow channel 16. After this, analyte solution or analyte fluid 27 as a fluid which contains analyte and fluid medium which may be solvent, is introduced into the flow channel 16. Again, the liquid buffer is introduced after the analyte fluid 27. Note that the flow channel 16 may be cleaned or washed before initially introducing the liquid buffer. Reading of data starts upon initially introducing the liquid buffer in order to detect a reference level of a signal. The reading is continued until the introduction of the liquid buffer at the second time after entry of the analyte fluid 27. It is possible not only to detect the reference level but to assay interaction or binding between the analyte and the ligand, and to measure a signal until dissociation between the analyte and ligand in response to introduction of the liquid buffer.

There are a measuring region (act) and a reference region (ref) formed in the linker film 22. The measuring region has immobilization of a ligand, and is a region for reaction between the ligand and analyte. The reference region does not have immobilization of a ligand, and is used for outputting a reference signal for comparison with a signal retrieved from the measuring region. Note that the reference region is formed in the course of film production of the linker film 22. An example of a process of the forming has steps of surface processing of the linker film 22 at first, and then deactivating the reaction groups in approximately a half of an entire area of the linker film 22 for binding with ligand. Thus, a half of the linker film 22 becomes the measuring region. A remaining half of the linker film 22 becomes the reference region.

The act-signal and ref-signal are measured simultaneously in the course of a period starting upon detection of a reference level, and then reaction of binding, and ending upon dissociation. Data analysis is effected by obtaining a difference or ratio of the act-signal and ref-signal. For example, the data analyzer 91 obtains data of a finite difference between the act-signal and ref-signal, and analyzes various items according to the finite difference. This makes it possible to cancel electric noise caused by external irregularities, such as individual specificity of sensor units or sensor cells, mechanical changes of the assay apparatus, temperature changes of the liquid, and the like. A signal with a high S/N ratio can be obtained.

Various liquids are available for use as the liquid buffer for assay, and solvent or diluent for the analyte fluid 27. Examples of the liquids include buffer liquids, or physiological saline water and other aqueous solutions of physiological salts, and pure water. It is possible according to a type of a ligand to determine suitably solution types and pH values of the solutions, and types of substances to be mixed, and their density. To facilitate dissolving of the analyte, dimethyl sulfoxide (DMSO) can be added to the physiological saline water. The use of the DMSO is reflected to a level of an output signal. The buffer for assay is used for detecting the reference level of the signal, as described above. If DMSO is contained in the solvent for the analyte, it is preferable to use buffer for assay at a DMSO density approximately equal to that of the solvent in the analyte.

In general, the analyte fluid 27 may be kept preserved for a long time, for example one year. It is likely that a difference occurs between an initial level and a current level of the DMSO density owing to a change with time. If assay with high precision is required, such a difference in the density is estimated according to the ref-signal level upon introducing the analyte fluid 27, so that measured data can be compensated for by DMSO density compensation. Compensation data for the DMSO density compensation is obtained before introducing the analyte fluid 27. A plurality of liquid buffers different in the DMSO density are introduced to the flow cells 17. Amounts of changes in the levels of ref-signal and act-signal are evaluated so as to obtain the compensation data.

An optical measuring unit or optical assay unit 31 is disposed in the assay apparatus 11. An illuminator 32 and a photo detector 33 are included in the optical assay unit 31. The reaction between the ligand and analyte can be recognized as a change of a resonance angle, which is an angle of incidence of light received by the thin film/dielectric interface 13b. To this end, the illuminator 32 is caused to apply light to the thin film/dielectric interface 13b at various values of angles of incidence satisfying a condition of the total reflection. The illuminator 32 includes a light source device 34 and an illuminating optical system 36, which includes a condensing lens, a diffusing plate and a polarizer. A position and angle of the installation of those elements are so determined that an angle of incidence of the light satisfies the condition of the above total reflection.

Examples of the light source device 34 include a light emitting diode (LED), laser diode (LD), super luminescent diode (SLD), and other light emitting element. A single element is used as the light source device 34 as a point light source. If simultaneous assay for plural sensor cells is described, light from a single light source can be separated to illuminate the plural sensor cells. Also, a plurality of elements as the light source device 34 may be arranged as a surface light source. The diffusing plate diffuses light from the light source device 34, and suppresses onset of irregularity in the light amount. The polarizer allows only p-polarized light to pass, the p-polarized light creating the surface plasmon resonance. Note that no polarizer is required if directions of rays emitted by the light source device 34, for example an LD, are kept equal. However, a diffusing plate may be combined with the light source device 34 of a type of which directions of emitted rays are kept equal. Directions of rays in polarization are changed unequal by the passage through the diffusing plate. For this structure, the polarizer can be utilized to set equal the directions of the rays. The light obtained after the diffusion and polarization is condensed by a condensing lens, and directed to the prism 14. It is possible to travel rays with various angles of incidence toward the thin film/dielectric interface 13b without irregularity in the intensity.

The photo detector 33 receives light reflected by the thin film/dielectric interface 13b, and detects intensity of the light. Rays of light are incident upon the interface 13b at various angles. It follows that light is reflected by the interface 13b at various angles of reflection according to the angles of the incidence. If there is a change in the resonance angle according to interaction of the analyte and ligand, a reflection angle at which light is attenuated is changed, too. An example of the photo detector 33 is a CCD area sensor, which retrieves such a change in the reflection angle as a gradual change in the attenuating position of the reflected light by a photo receptor surface. The photo detector 33 generates measured data which is information of the interaction, and sends the measured data to the data analyzer 91. The data analyzer 91 analyzes the measured data from the assay apparatus 11, to retrieve a characteristic and other information of the analyte.

Note that in FIG. 4, the illuminator 32 and the photo detector 33 in the optical assay unit 31 are positioned so that a direction of light projected and reflected between those intersects horizontally with a flow of the flow channel 16, which is unlike the structure depicted in FIG. 1B. The state of FIG. 1B is simplified for the convenience. However, in the invention the illuminator 32 and the photo detector 33 may be positioned according to in FIG. 1B so that a direction of light projected and reflected between those is horizontally aligned with the flow of the flow channel 16 between the pipettes.

Figure 2:
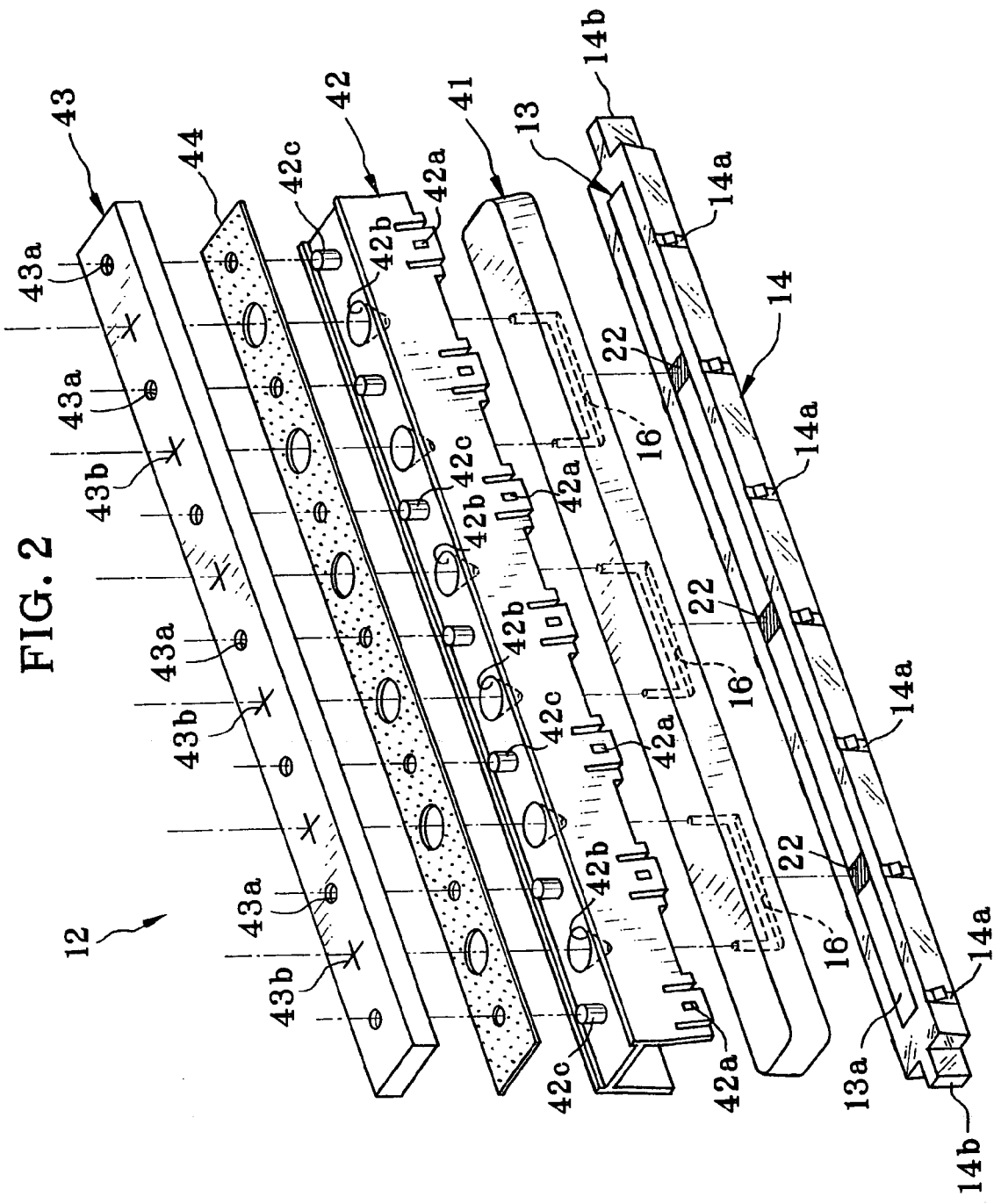
FIG. 2 is an exploded perspective illustrating a sensor unit.

In FIG. 2, the sensor unit 12 is illustrated structurally. The sensor unit 12 includes the flow channel block 41, the prism 14, a retaining block 42, and a lid 43. The flow channel block 41 has the at least one flow channel 16 formed through the same. The prism 14 has the metal film 13 overlaid on its upper surface. The retaining block 42 supports the flow channel block 41 by fitting its lower surface on an upper surface of the prism 14. The lid 43 is disposed higher than the retaining block 42.

The flow channel 16, for example three (3) channels, are formed in the flow channel block 41. The flow channel block 41 has a long shape, in which the flow channels 16 are arranged in a direction of a block length. The flow channels 16 constitute the sensor cells 17 together with the metal film 13 in connection with its lower surface. See FIGS. 1A and 1B. The flow channel block 41 is formed from elastic material for the purpose of ensuring tightness in contact with the metal film 13. Examples of elastic materials include rubber, polydimethylsilicone (PDMS), and the like. When a lower surface of the flow channel block 41 is pressed on an upper surface of the prism 14, the flow channel block 41 is elastically deformed, to remove a space between its surface and the metal film 13. Open lower portions of the flow channels 16 are closed water-tightly by the upper surface of the prism 14. Note that the number of the flow channels 16 may not be three, but can be one or two, or four or more.

The metal film 13 is deposited on the prism 14 by vapor deposition. The metal film 13 is formed in plural regions of long quadrilaterals opposed to the flow channel 16 formed in the flow channel block 41. Also, the linker film 22 is overlaid on an upper face or the sensing surface 13a of the metal film 13 and in regions associated with the flow channels 16. Retaining claws 14a are formed to project from the prism 14 at its sides as viewed longitudinally. Retaining claws 42a of the retaining block 42 are engageable with the retaining claws 14a. The flow channel block 41 is sandwiched between the retaining block 42 and the prism 14. A lower surface of the flow channel lock 41 is kept fitted on the prism 14. A composite part as biosensor is obtained by unifying the flow channel block 41, the metal film 13 and the prism 14.

Retaining projections 14b protrude from ends of the prism 14 as viewed in its longitudinal direction. A sensor holder 52 of FIG. 3 contains a plurality of sensor units 12. As will be described later, the immobilization on the sensor unit 12 is effected while the sensor unit 12 is contained in the sensor holder 52. The retaining projections 14b are formed for positioning the sensor unit 12 in a contained state by engagement with the sensor holder 52.

A receiving orifice 42b is formed in the retaining block 42, and positioned at each of the entrance end opening 16a and the exit end opening 16b of the flow channel 16, for entry of an end of each of dispensing and removing pipettes 26a and 26b and the dispensing and removing pipettes 19a and 19b. The receiving orifice 42b has a funnel shape for introducing liquid ejected by the pipettes toward the entrance end opening 16a. When the retaining block 42 is retained on the prism 14 with the flow channel block 41, a lower side of the receiving orifice 42b is connected with the entrance end opening 16a and the exit end opening 16b, for communication of the receiving orifice 42b with the flow channel 16.

Cylindrically shaped bosses 42c are formed to project beside the receiving orifice 42b. Positioning holes 43a are formed in the lid 43. The bosses 42c are fitted in the positioning holes 43a, to position the lid 43 firmly. Double-sided adhesive tape 44 attaches the lid 43 to an upper surface of the retaining block 42. Note that suitable holes are formed in the double-sided adhesive tape 44 and associated with the receiving orifice 42b and the bosses 42c.

The lid 43 covers the receiving orifice 42b communicating to the flow channel 16, and prevents evaporation of liquid in the flow channel 16. The lid 43 is formed from rubber, elastomer, resin or other elastic material. A cross shaped slit 43b is formed in the lid 43 and positioned respectively at the receiving orifice 42b. The lid 43 is required to cover the receiving orifice 42b in order to prevent liquid in the flow channel 16 from evaporation. However, no pipette can enter the receiving orifice 42b if covering of the lid 43 is complete. So the cross shaped slit 43b is formed to enable insertion of pipettes, and to close the receiving orifice 42b while no pipette is inserted. If a pipette is forcibly pressed into the cross shaped slit 43b, its edges are elastically deformed, to allow receipt of the pipette by becoming open. See FIGS. 1A and 1B. When the pipette is externally pulled out, the cross shaped slit 43b elastically closes the receiving orifice 42b again by returning to its initial state.

Figure 3:
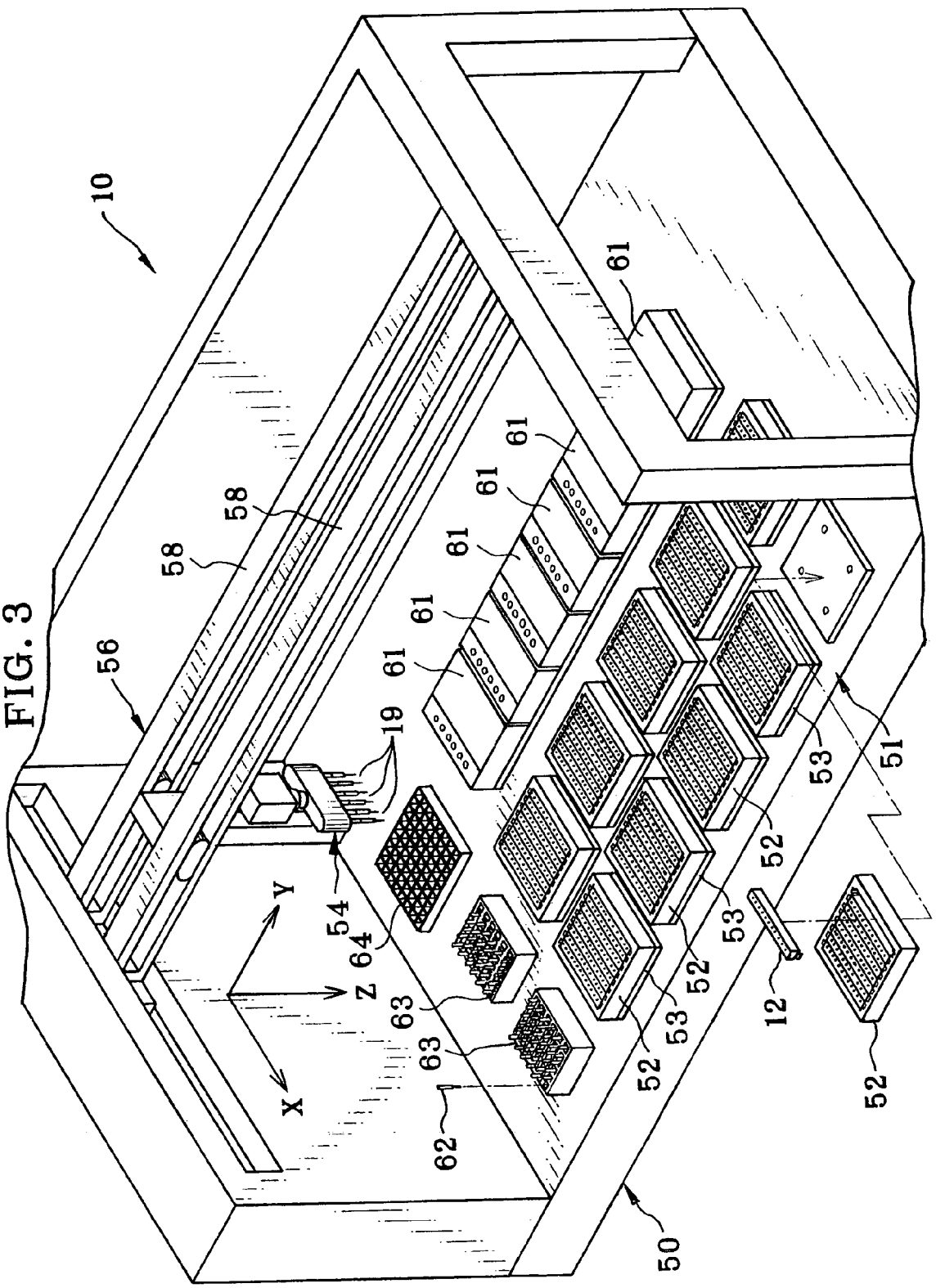
FIG. 3 is a perspective view, partially broken, illustrating a sample immobilizing device.

In FIG. 3, a casing base 50 is included in the sample immobilizing device 10. An immobilizing stage 51 of the sample immobilizing device 10 is formed on the casing base 50 so as to place the sensor unit 12 thereon. While the immobilizing stage 51 supports the sensor unit 12, the entirety of the immobilizing process is effected. Thus, the immobilizing stage 51 is a principal section operating for the sensor unit 12.

The sensor unit 12 is set in the sample immobilizing device 10 in a state contained in the sensor holder 52. For example, eight (8) of the sensor units 12 can be contained in the sensor holder 52. The retaining projections 14b of the sensor unit 12 are engaged with engageable portions of the sensor holder 52, which positions the sensor unit 12. Also, a lower side of the sensor holder 52 is open except for a region for supporting ends of the sensor unit 12. If removal of the sensor unit 12 from the sensor holder 52 is desired in the assay process, the open side of the sensor holder 52 is accessed, as will be described later. A shifting element 81a of FIG. 4 is inserted in the open side, to push up the sensor unit 12.

The immobilizing stage 51 is so large that ten of the sensor holders 52 can be installed at one time there. Plural pallets 53 are disposed in the immobilizing stage 51. Positioning bosses are formed on each of the pallets 53 for positioning the sensor holder 52.

A pipetting head group 54 with a fluid transfer mechanism is disposed in the sample immobilizing device 10, and includes pipetting heads of the three pipette couples 19 for combination with pipette tips. The pipetting head group 54 accesses the sensor unit 12 in a conveyor belt 55 to introduce and discharge fluid. As the pipette couples 19 are three pairs in the pipetting head group 54, three of the sensor cells 17 can be accessed in the sensor unit 12 for the introduction or discharge of liquid at the same time. A controller in the sample immobilizing device 10 controls the pipetting head group 54 for operation of the pipette couples 19 regarding various items, for example an amount of fluid in dispensation or suction, and a time sequence of the dispensation or suction.

A pipetting head moving assembly 56 on the casing base 50 moves the pipetting head group 54 in the three directions of X, Y and Z. An example of the pipetting head moving assembly 56 is constituted by elements including a transporting belt, pulley, carriage, motor and other well-known devices. The pipetting head moving assembly 56 includes a vertical shifter, a first horizontal shifter and a second horizontal shifter. The vertical shifter moves the pipetting head group 54 up and down. The first horizontal shifter includes guide rails 58, which keep the pipetting head group 54 movable in the direction Y together with the vertical shifter. The second horizontal shifter supports the guide rails 58 at two ends, and moves the pipetting head group 54 in the direction X together with the guide rails 58. The controller controls the pipetting head moving assembly 56, and controls the vertical position and horizontal position of the pipetting head group 54 by driving the pipetting head moving assembly 56.

Plural fluid reservoirs 61 are disposed on the casing base 50 for storing various fluids to be supplied to the flow channel 16, the fluids including ligand fluid, washing liquid, liquid buffer for immobilization, evaporation retardant or evaporation inhibitor, activating liquid, blocking liquid and the like. The number of the fluid reservoirs 61 is determined according to the number of the types of liquid in use. Six insertion orifices are formed in the fluid reservoirs 61. The number and interval of the orifices are determined according to the number of pipettes associated with the pipetting head group 54 and their interval. The pipetting head group 54, for introduction of the liquid into the sensor cells 17, accesses the fluid reservoirs 61 to suck liquid, and then moves to the immobilizing stage 51 for introduction to the sensor unit 12.

A pipette tip tray or rack 63 is placed on the casing base 50. Pipette tips 62 are stored in the pipette tip tray 63. The pipette tips 62 are fitted on ends of pipetting heads of the dispensing and removing pipettes 19a and 19b in a removable manner. As the pipette tips 62 come in direct contact with liquid, the pipette tips 62 are exchanged for respective types of fluids in use so as not to prevent mixture or contamination of the fluids. Each of the dispensing and removing pipettes 19a and 19b is composite pipette equipment, which has a mechanism for automatically picking up and releasing the pipette tips 62 so as to renew the pipette tips 62 without manual operation. If renewal of the pipette tips 62 is desired, at first the pipetting head group 54 releases a used one of the pipette tips 62 by use of an abandoning unit (not shown). Then the pipetting head group 54 accesses the pipette tip tray 63 to pick up unused ones of the pipette tips 62.

There is a well plate 64 having a plurality of wells arranged in a matrix form. The well plate 64 is used for storing fluid retrieved by the pipettes in a preliminary manner, and also for mixing a plurality of fluids to prepare liquid composition.

For the immobilization, the casing of the sample immobilizing device 10 is covered by a cover (not shown), which intercepts the inside of the sample immobilizing device with the immobilizing stage 51 from the outside. A temperature adjuster (not shown) keeps the temperature of the inside of the sample immobilizing device 10 adjustable. The sensor unit 12 remains set on the immobilizing stage 51 for a certain time after introduction of ligand on the sensor cells 17 and before completing the immobilization of the ligand 21a on the sensing surface 13a. In the course of preservation, the ligand fluid 21 is stirred or turbulently flowed in the flow channel 16 if required. The extent of immobilization depends upon temperature or other environmental conditions of the sensor unit 12. Thus, the temperature adjuster is used to keep the inside of the sample immobilizing device 10 at a predetermined temperature. The temperature and time for keeping the sample immobilizing device 10 are suitably determined according to a type of the ligand 21a.

When the immobilization is completed, liquid buffer is introduced as washing liquid. While the sensor cells 17 are filled with the ligand solution or ligand fluid as a fluid which contains ligand and fluid medium, the pipette 19a with the liquid buffer is inserted in the cross shaped slit 43b to introduce the liquid buffer to the sensor cells 17. When the liquid buffer, is ejected from the entrance end opening 16a to flow into the flow channel 16, the ligand fluid having been filled in the flow channel 16 is pressurized toward the exit end opening 16b, and discharged from the flow channel 16. The pipette 19b is controlled for suction in synchronism with the pipette 19a in the dispensation. The pipette 19b retrieves the ligand fluid by suction at the same time as the supply of the liquid buffer. As a result, what is filled in the sensor cells 17 is changed over.

After completion of washing, evaporation retardant for the ligand 21a is introduced to the sensor cells 17 in the same manner as above. The evaporation retardant substitutes for the fluid buffer. The sensor unit 12 is transferred to the assay apparatus 11 together with the sensor holder 52 and with the ligand 21a on the sensing surface 13a kept humid by the evaporation retardant. The ligand 21a can be prevented from drying before the start of the measurement.

Various fluids are available for use as the evaporation retardant. Examples of the evaporation retardant include buffer liquids, or physiological saline water and other aqueous solutions of physiological salts, and pure water. It is possible according to a type of a ligand to determine suitably solution types and pH values of the solutions, and types of substances to be mixed, and their density. An amount of the evaporation retardant is sufficient when the ligand 21a of the sensing surface 13a is wetted at all with the evaporation retardant because drying of the ligand 21a can be prevented. However, it is preferable to use a greater amount than enough to wet the ligand 21a, for example to fill the flow channel 16 with the evaporation retardant, which is in consideration of reduction of the evaporation retardant by evaporation of itself.

In FIG. 4, the assay apparatus 11 includes a holder moving mechanism 71, a sensor setting pickup mechanism 72 or sensor setting mechanism, a pipetting head moving assembly 73, and an assay stage 74. A casing 75 of the assay apparatus 11 accommodates those elements. The holder moving mechanism 71 includes a transporting belt 76, a carriage 77 and a pallet 78. The carriage 77 is secured on the transporting belt 76. The pallet 78 is secured to the carriage 77, and supports the sensor holder 52 containing the sensor unit 12 after the immobilization. The holder moving mechanism 71 shifts the pallet 78 in the direction X together with the sensor holder 52, to set each of the sensor units 12 to a pickup position for the sensor setting pickup mechanism 72 to pick up.

The sensor setting pickup mechanism 72 to access the sensor unit 12 from the sensor holder 52 includes a pressing shifter 81 and a handling head or chuck 82. The pressing shifter 81 presses up the sensor unit 12 contained in the sensor holder 52. The handling head 82, when the sensor unit 12 is pressed up by the pressing shifter 81, squeezes and holds the sensor unit 12. A middle of the sensor holder 52 has a holder opening. A middle of the support panel or pallet 78 has an opening associated with the holder opening. The pressing shifter 81 includes the shifting element 81a and a shifter driving mechanism 81b. The shifting element 81a moves from a lower side of the pallet 78 and upwards to come through the pallet 78, and contacts a lower surface of the sensor unit 12 by entry through the sensor holder 52 to push up the sensor unit 12. The shifter driving mechanism 81b drives the shifting element 81a to move up and down.

The handling head 82 includes two segments for squeezing the sensor unit 12. A head body or chuck body 82a is a base of the handling head 82. A ball screw 86 in a sensor setting mechanism extends beside the handling head 82. A nut 84 between the handling head 82 and the ball screw 86 keeps the handling head 82 movable in response to rotations of the ball screw 86. The handling head 82 is movable in the direction Y, to transfer the sensor unit 12 to the assay stage 74. After the assay, the handling head 82 moves back to the pickup position, and releases the sensor unit 12 being used to drop back to the sensor holder 52.

In the assay stage or signal detecting stage 74 are disposed the illuminator 32 and the photo detector 33 under a level where the sensor unit 12 is disposed. The sensor unit 12 includes a plurality of the sensor cells 17, for each of which biomaterial is assayed. The assay stage 74 moves the sensor unit 12 in the direction Y at an amount of the pitch of the sensor cells 17 arranged regularly, to shift each of the sensor cells 17 into a light path of the illuminator 32 suitably.

As has been referred to above, the illuminator 32 and the photo detector 33 are positioned so that a direction of light projected and reflected between those for the sensor unit 12 intersects horizontally with a flow of the flow channel 16, which is depicted in FIG. 4.

A pipetting head group 87 with a fluid transfer mechanism is transferred by the pipetting head moving assembly 73. The pipetting head group 87 includes the pipette couple 26, and shifted in the directions X, Y and Z. A table or pallet 92 supports three well plates or fluid reservoirs 88, 89 and 90 as fluid feeder or fluid processor. The pipetting head group 87 is moved between the pallet 92 and the sensor unit 12 in the assay position. The pipetting head moving assembly 73 is structurally the same as the pipetting head moving assembly 56 of the sample immobilizing device 10. The pipetting head group 87 has the pipette driving mechanism or fluid transfer mechanism, connected with the pipette heads of the pipette couple 26. The fluid transfer mechanism causes dispensation and suction through the dispensing and removing pipettes 26a and 26b.

A mechanical controller 85 controls the holder moving mechanism 71, the sensor setting pickup mechanism 72, the pipetting head moving assembly 73 and the pipetting head group 87 which are included in the assay apparatus 11. For the assay, the mechanical controller 85 causes the pipetting head group 87 to access the pallet 92 so the dispensing pipette sucks the analyte fluid 27 at a prescribed amount. Then the mechanical controller 85 moves the pipetting head group 87 to the assay stage 74, to introduce the analyte fluid 27 to a designated one of the sensor cells 17. The pipetting head group 87 accesses the sensor unit 12, and introduces and removes fluids. The pipette couple 26 is only one pair of pipettes unlike the pipetting head group 54 in the sample immobilizing device 10, because only the particular one of the sensor cells 17 is accessed by the pipetting head group 87.

The three well plates or fluid reservoirs 88, 89 and 90 are placed on the pallet 92, and respectively include plural wells disposed in a matrix form for storing fluids. The analyte well plate 88 as fluid feeder or fluid processor is an analyte reservoir for storing the analyte fluid 27. The analyte well plate 88 is a multi-purpose type in which a number of types of the analyte fluid 27 are stored in the wells. The diluent well plate 89 is a diluent reservoir for storing diluent liquid to dilution of the density of the analyte fluid 27. The mixing well plate 90 is a mixing section for mixing the analyte fluid 27 with the diluent liquid for lowering the density. Note that fluid reservoirs for measuring buffer and washing liquid are disposed in the assay apparatus 11 for being accessed by the pipette couple 26. A pipette tip reservoir is used for containing pipette tips for exchange.

Figure 5:
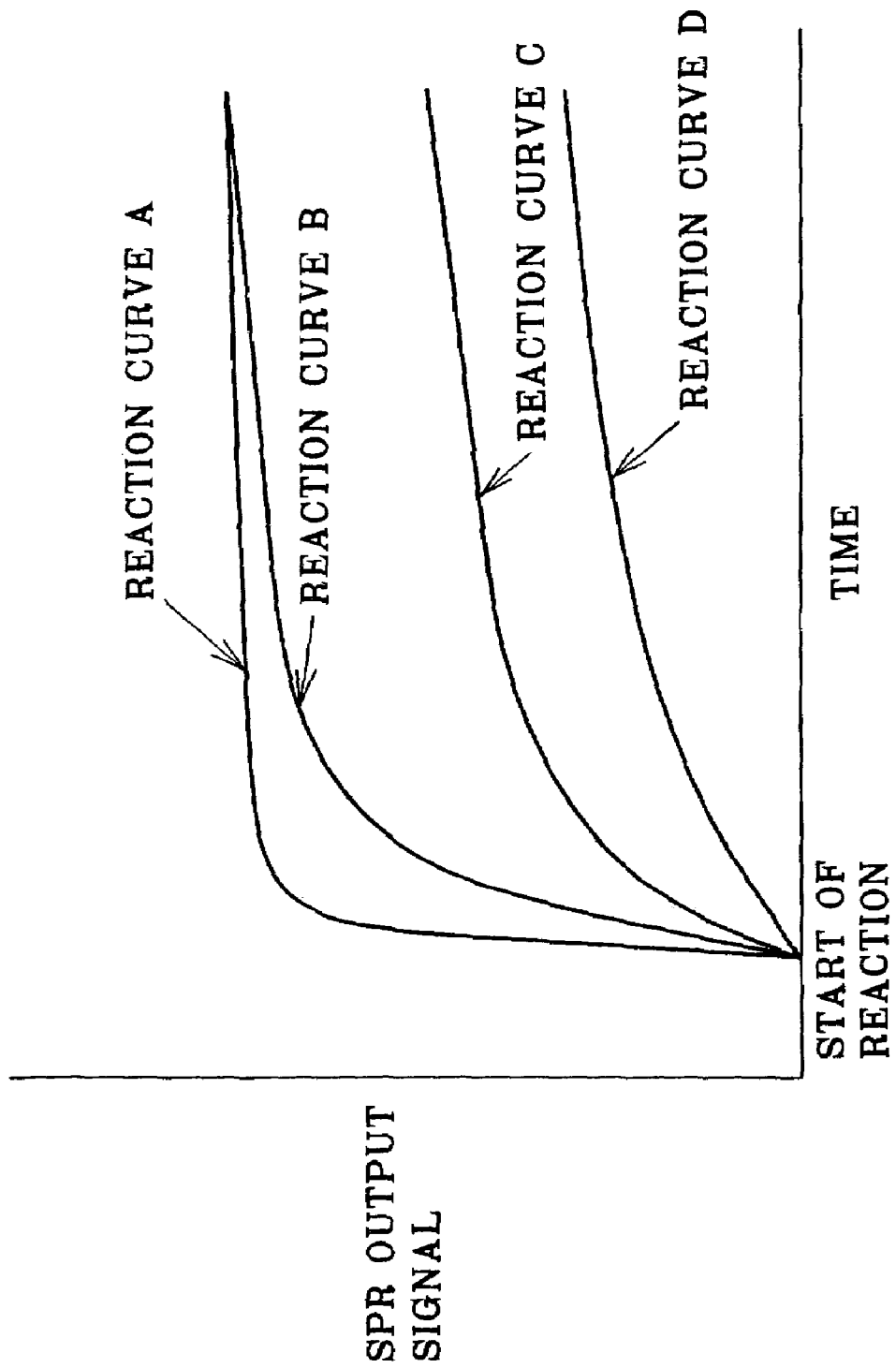
FIG. 5 is a graph illustrating a relationship between time and an output signal of the biosensor.

As has been described heretofore, the curve fitting is used in analyzing the measured data for the purpose of obtaining a reaction speed constant of the speed of the reaction of the analyte. Reaction curves are required for the curve fitting in suitable curved forms. In FIG. 5, reaction curves of analyte fluids of plural density values are illustrated in a graph. Curve A has the highest density. Curves B and C have second and third highest densities. Curve D has the lowest density. A gradient of the signal level of curve A is high in an initial section of the reaction, but is gradually lower in a section succeeding to this. The positive value of the gradient of the signal level is lower according to the low state of the density. Together with this, an absolute value of the signal level is lower. Curves A-D are all related with recognizable reaction on ligand. However, a certain unknown substance does not react on the ligand, to have a constant level of an output signal without changes. In short, the shape of the curves is different according to the density. It is empirically known that the shape of the reaction curve suitable for the curve fitting has a gradient of an early stage of the reaction which gradient must be within a limited range.

For the purpose of assaying an unknown compound, at first analyte fluid of a high density is used to check whether the compound reacts on the analyte fluid. If reaction occurs, then the analyte fluids of gradually lowered densities are used for evaluating assay, to obtain reaction curves suitable for curve fitting. The assay apparatus 11 changes the density of the analyte fluid 27 stepwise in a decreasing manner. The measurement is automatically repeated until an optimized reaction curve is obtained.

The density of the analyte fluid 27 is adjusted by the access of the pipetting head group 87 to the well plates 88, 89 and 90 prior to the evaluating assay. To lower the density the analyte fluid 27, at first the pipetting head group 87 accesses the analyte well plate 88 for the dispensing pipette to suck the analyte fluid 27 at a prescribed amount, and transfers the analyte fluid 27 to a particular well in the mixing well plate 90. Then the pipetting head group 87 accesses the diluent well plate 89 for the dispensing pipette to suck a diluent liquid at a prescribed amount, and ejects the diluent liquid to the particular well in the mixing well plate 90 having provided with the analyte fluid 27. Thus, the analyte fluid 27 at a target density is prepared.

When the evaluating assay is made, measured data or SPR signal output by the photo detector 33 is transmitted to the data analyzer 91. The data analyzer 91 analyzes interaction between the analyte and ligand according to the measured data.

Figure 6:
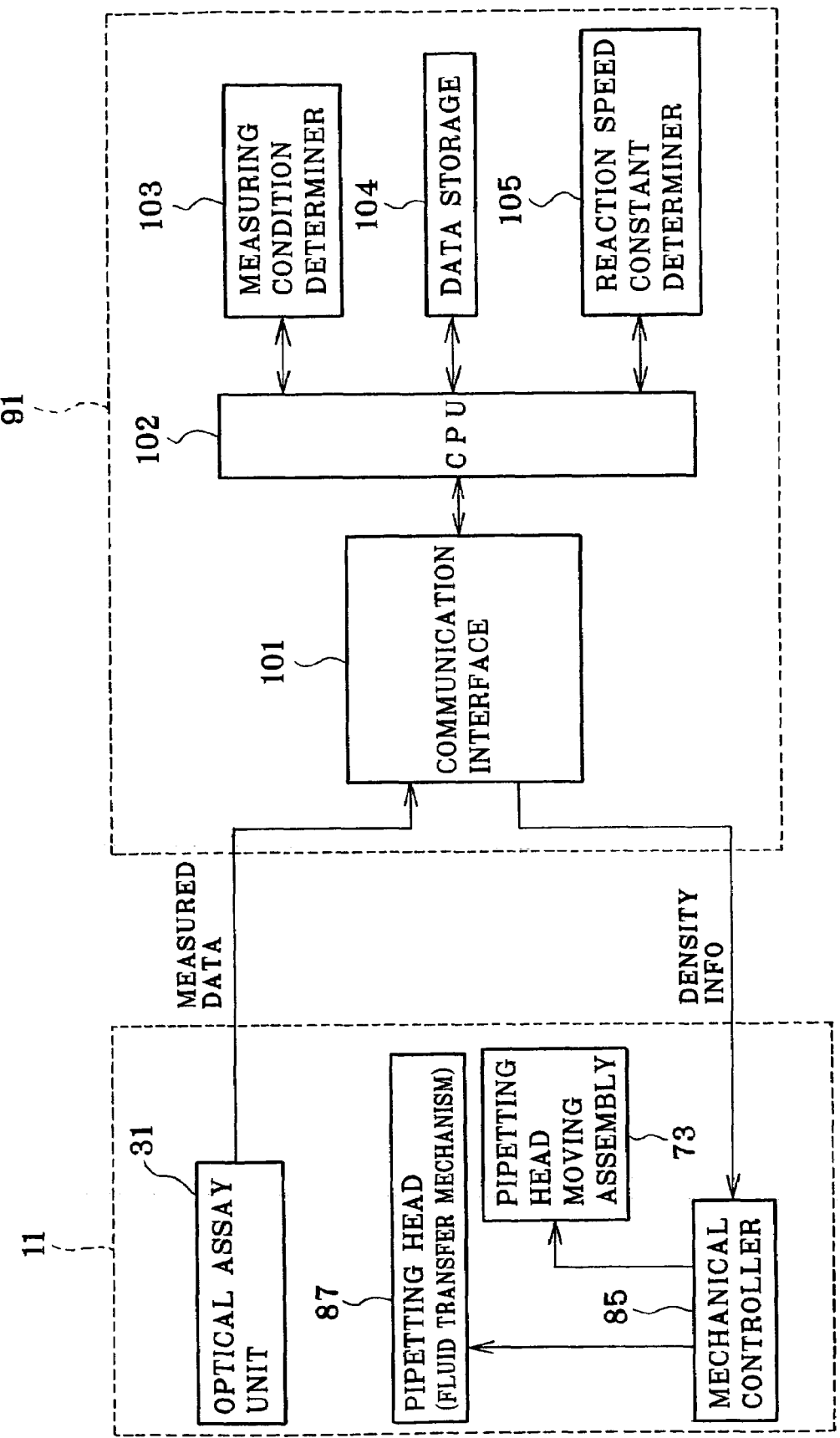
FIG. 6 is a block diagram illustrating circuitry in a data analyzer.

In FIG. 6, the data analyzer 91 includes a communication interface (I/F) 101, a CPU 102 as evaluator, a measuring condition determiner 103, a memory or data storage 104, a reaction speed constant determiner 105 and a monitor display panel 106. The CPU 102 controls elements in the data analyzer 91, analyzes measured data output by the assay apparatus 11, and also instructs the optical assay unit 31 for assay. The CPU 102 controls the relevant elements in the assay apparatus 11 for introduction of the analyte fluid 27 to the sensor unit 12, and preparation of the analyte fluid 27 at a determined density. The communication interface 101 is a device for connection between the data analyzer 91 and the assay apparatus 11 for transmission of the measured data and control signals.

In the data analysis, the CPU 102 as evaluator checks whether the measured data is suitable to the curve fitting. Examples of the data storage 104 are a RAM, ROM, HDD and the like, and as a work memory for storing a control program for execution in the CPU 102, and other programs.

The data storage 104 stores a reference parameter for being referred to when the CPU 102 determines suitability of measured data for the curve fitting. An example of the reference parameter is a gradient of a reaction curve in an increasing direction in one initial section of the curve. At first, the CPU 102 creates a reaction curve according to the measured data obtained by the optical assay unit 31, and derives the gradient in the initial section of the curve. Let A be the gradient actually measured by the evaluating assay. Let B be the reference gradient in an allowable value stored as reference parameter. The CPU 102 compares the retrieved gradient A with the reference gradient B, and if a difference between those is within a prescribed range, then judges that the measured data is suitable for the curve fitting. If the difference is out of the prescribed range, the CPU 102 judges that the measured data is unsuitable. If the measured gradient A is zero (0), a result of lack of reaction of the analyte on the ligand is obtained and displayed on the monitor display panel 106. Evaluating assay succeeding to this is discontinued.

If the CPU 102 as evaluator judges that the measured data is unsuitable, then the measuring condition determiner 103 determines a second density of the analyte fluid 27 as a condition of next measurement. The measuring condition determiner 103 multiplies the first density of the analyte fluid 27 by a value of a ratio B/A to obtain a second density. For example, the density D1 of the first time is 2%. Let the measured gradient A be 10 after the evaluating assay. Let the reference gradient B be 5. In consideration of the D2=D1×B/A, the second density D2 is $$D2=2\%\times 5/10=1\%.$$

The obtained density information or evaluated condition is transmitted by the communication interface 101 to the assay apparatus 11. The CPU 102 in addition to the transmission instructs the assay apparatus 11 to prepare the analyte fluid 27 at the determined density, and to evaluate the analyte fluid 27 being prepared. The assay apparatus 11 responsively prepares and assays the analyte fluid 27, and outputs obtained second measured data to the data analyzer 91. The processes of the preparation of the analyte fluid 27 at the determined density and assay are repeated until the CPU 102 obtains measured data optimized for the curve fitting. The constant determiner 105 operates for curve fitting according to the measured data, and generates data of a reaction speed constant. Characteristics of the analyte are analyzed according to the obtained reaction speed constant.

Figure 7:
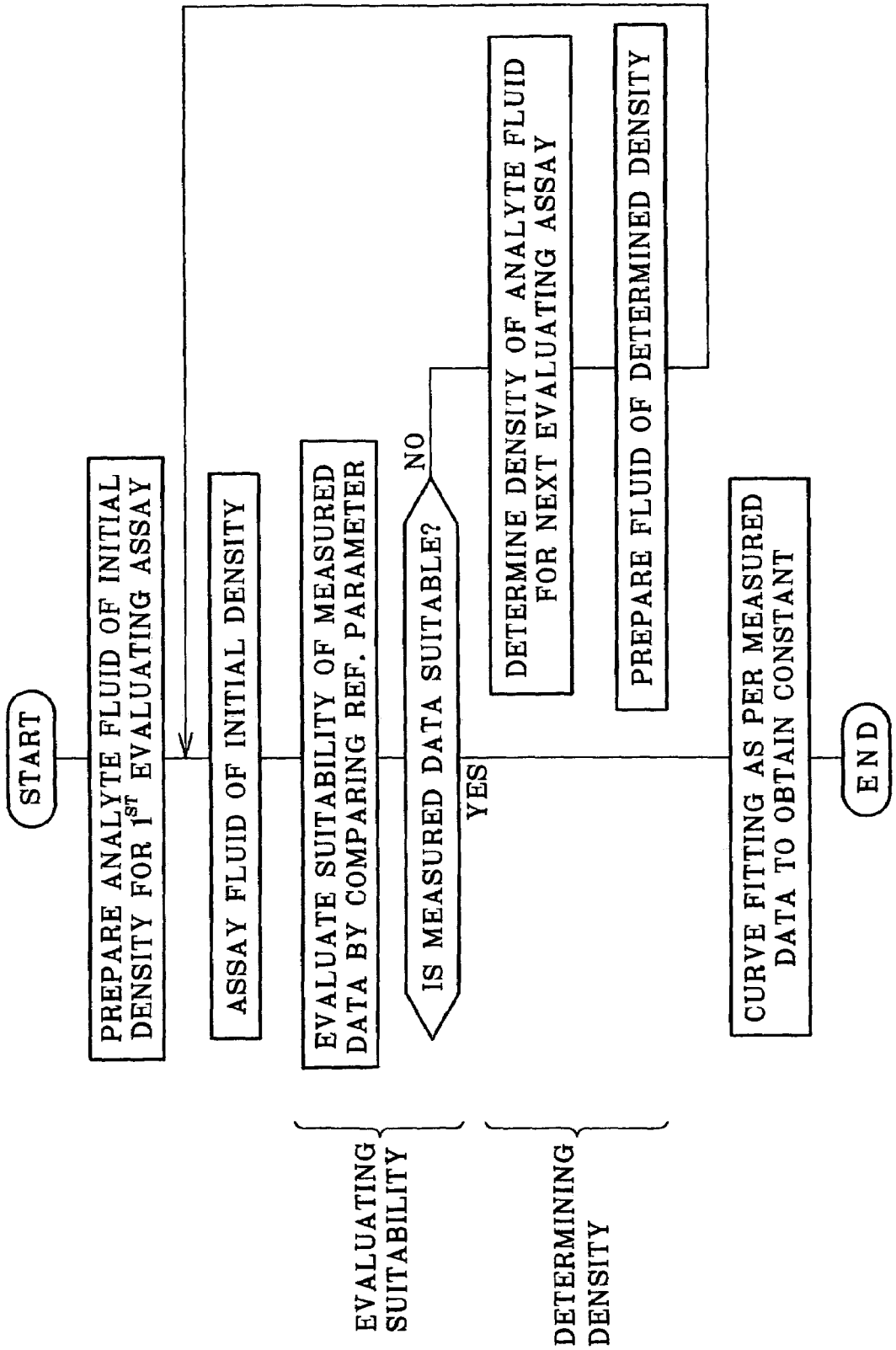
FIG. 7 is a flow chart illustrating a process of obtaining measured data suitable for curve fitting.

The operation of the invention is described by referring to the flow in FIG. 7. The data analyzer 91 instructs the assay apparatus 11 to evaluate by assay at a first time. Density of the analyte fluid 27 used in the first evaluation is given previously. The pipetting head group 87 causes the dispensing pipette to provide the analyte fluid 27 at this initial density. Measured data is obtained by evaluating assay with the analyte fluid 27. The assay apparatus 11 outputs and transmits the measured data to the data analyzer 91. The CPU 102 judges the suitability of the measured data according to the above processes. The measured data, if determined suitable, is transmitted to the reaction speed constant determiner 105. Curve fitting is conducted by the constant determiner 105 on the basis of the measured data, to obtain the reaction speed constant.

In contrast, if the measured data is determined unsuitable, then the measuring condition determiner 103 determines information of a second density to be used in next evaluating assay. The second density information is sent to the assay apparatus 11. The assay apparatus 11 prepares the analyte fluid 27 at the density according to the density information being input, and evaluates for the second time by assay with the analyte fluid 27 being adjusted. Second measured data is obtained, and transmitted to the data analyzer 91. The data analyzer 91 checks the second measured data for suitability, and if the second measured data is judged suitable, then calculates a reaction speed constant.

If the measured data is determined unsuitable, then second evaluating assay is made for determining density. The assay apparatus 11 is instructed by the data analyzer 91 to adjust the density of the analyte fluid 27 for evaluating assay. The determination and evaluating assay is cyclically repeated until suitable measured data is obtained finally.

It is possible to automate a sequence of various processes, which include checking suitability of measured data for reaction curves allowed for the curve fitting, determining a second density of the analyte fluid in the case of lack of the suitability, preparing the analyte fluid at the determined density, and measuring again the analyte fluid being prepared. The determination of the reaction curves which has been made by discrete steps and respective technicians conducting experiments is remarkably facilitated. Also, the automation can prevent errors in observation, estimation and calculation of the technicians. Time for experiments can be shortened. Errors in the analysis can be avoided.

In the present embodiment, the gradient of the reaction curve is checked as reference parameter for determining the suitability of the measured data. However, a reference parameter may other characteristics, for example an absolute value of a level of the output signal in an early section of the reaction, length of time required until stabilization of a level of the output signal.

In the above embodiment, the determination of suitability of the measured data is repeated until optimized measured data is obtained. However, determination of suitability may be only at one time. This is advantageous in simplifying the processes before obtaining suitable density owing to the one time of the determination.

In the above embodiment, the sensor unit is a composite structure including the metal ilm, low channel and prism. However, no prism may be included in a sensor unit. Instead, a prism can be included in a main unit of the assay apparatus. Furthermore, a sensor unit according to the invention may be different from that including the metal film and flow channel, for example, can be a chip type having a sensor chip.

Although the casing for the assay apparatus is separate from the casing for the data analyzer according to the above embodiment, a single casing can be used for installing both the assay apparatus and the data analyzer. Instead of determining the region of the reaction speed constant determiner 105 in the data analyzer, it is possible to constitute the constant determiner 105 by use of external computer or electronic equipment in connection with the data analyzer.

In the above embodiment, the density of the analyte fluid is determined again to measure interaction of this and the ligand. Furthermore, it is possible by use of the novel feature of the invention to measure reaction of a selected one of the ligand and analyte on the sensing surface.

In addition to the SPR sensor, an assay sensor according to the invention can be other sensor in utilizing attenuated total reflection. One example of sensor according to utilizing the attenuated total reflection is a leaky mode sensor. The leaky mode sensor includes a dielectric medium, a cladding layer overlaid on the dielectric medium, and an optical waveguide layer overlaid on the cladding layer, those layers constituting a thin film. A first surface of the thin film is a sensing surface on the optical waveguide layer. A second surface of the thin film is a thin film/dielectric interface on the cladding layer. When light becomes incident on the thin film/dielectric interface to satisfy the condition of the total reflection, part of the light passes through the cladding layer, and enters the optical waveguide layer. A guided mode to propagate light is excited responsively in the optical waveguide layer, to attenuate the reflected light on the thin film/dielectric interface. An angle of the incidence at which the guided mode is excited is changeable according to the refraction index of the medium positioned on the sensing surface. This is similar to the characteristic of the resonance angle of the SPR sensor. The attenuation of the reflected light is detected, so that it is possible to measure the interaction on the sensing surface.

Although the present invention has been fully described by way of the preferred embodiments thereof with reference to the accompanying drawings, various changes and modifications will be apparent to those having skill in this field. Therefore, unless otherwise these changes and modifications depart from the scope of the present invention, they should be construed as included therein.

What is claimed is:

1. An assay apparatus utilizing attenuated total reflection comprising:
    a sensor unit, said sensor unit including a transparent dielectric medium and a thin film, having a first surface and a sensing surface reverse thereto, said first surface overlying on said dielectric medium to constitute a thin film/dielectric interface, said sensing surface causing reaction of sample fluid;
    an optical assay unit for applying illuminating light to said interface through said dielectric medium in such a form as to satisfy a total reflection condition and for deriving information of reaction of said sample fluid by detecting said illuminating light reflected by said interface;
    a fluid processor for preparing said sample fluid at a density by mixing with diluent fluid;
    an evaluator, responsive to an evaluating assay in using said sample fluid prepared by said fluid processor, for comparing measured data output by said optical assay unit with a reference parameter stored in a data storage, in order to evaluate suitability of said measured data for analysis; and
    a density determiner, responsive if said evaluator estimates lack of said suitability, for determining a succeeding density of said sample fluid to be used in a succeeding evaluating assay according to said measured data with said estimated lack of said suitability;
    wherein said fluid processor prepares said sample fluid at said succeeding density determined by said density determiner, for said succeeding evaluating assay according to said succeeding density of said sample fluid.

2. An assay apparatus as defined in claim 1, wherein said sample fluid comprises analyte, and said sensing surface causes interaction of ligand with said analyte.

3. An assay apparatus as defined in claim 1, further comprising a controller, in operation until said evaluator judges that said measured data from said optical assay unit is suitable, for repeatedly carrying out said evaluating assay with said sample fluid at said density determined by said density determiner.

4. An assay apparatus as defined in claim 3, wherein said sensor unit includes plural sensor cells, each of which is constituted by said sensing surface and a flow channel for flow of said sample fluid on said sensing surface, and said sensor cells are subjected to said evaluating assay discretely from one another.

5. An assay apparatus as defined in claim 4, further comprising a constant determiner, responsive if said evaluator estimates said suitability, for determining a reaction speed constant of said sample fluid by curve fitting according to said measured data with said suitability.

6. An assay apparatus as defined in claim 5, wherein said fluid processor includes:
    a sample fluid reservoir for storing said sample fluid;
    a diluent reservoir for storing said diluent fluid; and
    a mixer for accessing said sample fluid reservoir and said diluent reservoir and for producing mixture thereof.

7. An assay apparatus as defined in claim 5, wherein said reference parameter comprises a gradient of a reaction curve optimized for said curve fitting.

8. An assay apparatus as defined in claim 7, wherein said evaluator compares said reference parameter with a gradient of a reaction curve created according to said measured data, to estimate suitability of said measured data.

9. An assay apparatus as defined in claim 8, wherein said density determiner considers a gradient A—defined as gradient actually measured by said evaluating assay—of said reaction curve according to said measured data, and a gradient B—defined as an allowable value stored as said reference parameter—and determines said succeeding density by multiplying said density by a value of a ratio B/A.

10. An assay apparatus as defined in claim 5, wherein said reference parameter comprises at least one selected from a gradient of a reaction curve, an absolute value of a signal level in an initial step in reaction, and time required for creating a stable state of said signal level.

11. An assay apparatus as defined in claim 4, wherein said sensor unit further includes:
    a flow channel block, having a flow channel, oriented to receive said sensing surface at said flow channel, for causing said sample fluid to flow on said sensing surface upon being introduced;
    a prism, positioned between said flow channel block and said optical assay unit, for constituting said transparent dielectric medium, and for passing said illuminating light reflected by said interface in said total reflection.

12. An assay apparatus as defined in claim 4, wherein said thin film is metal film, and is responsive to incidence of said illuminating light, to generate surface plasmon resonance on said sensing surface.

13. An assay method utilizing attenuated total reflection comprising:
    a reacting step of causing reaction of sample fluid on a sensing surface formed in a sensor unit including a transparent dielectric medium, and thin film, having a first surface and said sensing surface reverse thereto, said first surface overlying on said dielectric medium to constitute a thin film/dielectric interface;
    a detection step of applying illuminating light to said interface through said dielectric medium in such a form as to satisfy a total reflection condition and deriving information of reaction of said sample fluid by detecting said illuminating light reflected by said interface;

an outputting step of outputting measured data from said detection step;

an evaluating step of comparing said measured data with a reference parameter stored in a data storage, in order to evaluate suitability of said measured data for analysis;

a density determining step of, if lack of said suitability is estimated in said evaluating step, determining a succeeding density of said sample fluid to be used in a succeeding evaluating assay according to said measured data with said estimated lack of said suitability; and a fluid preparing step of preparing said sample fluid at said succeeding density by mixing with diluent fluid;

wherein said sample fluid prepared in said fluid preparing step is used for said succeeding evaluating assay.

14. An assay method as defined in claim 13, wherein until it is judged in said evaluating step that said measured data from said optical assay unit is suitable, said evaluating assay with said sample fluid is repeatedly carried out at said density determined in said density determining step.

15. An assay method as defined in claim 14, wherein said sensor unit includes plural sensor cells, each of which is constituted by said sensing surface and a flow channel for flow of said sample fluid on said sensing surface, and said sensor cells are subjected to said evaluating assay discretely from one another.

16. An assay method as defined in claim 15, further comprising a constant determining step of, if said suitability is estimated in said evaluating step, determining a reaction speed constant of said sample fluid by curve fitting according to said measured data with said suitability.

17. An assay method as defined in claim 15, further comprising steps of:

moving one of said sensor unit and a fluid dispenser relative to a remaining one thereof;

setting said fluid dispenser at one of said sensor cells in said sensor unit; and introducing said sample fluid after being prepared to said one sensor cell through said fluid dispenser.

18. An assay method as defined in claim 13, wherein said thin film is metal film, and is responsive to incidence of said illuminating light, to generate surface plasmon resonance on said sensing surface.

* * * * *